US012753151B2

(12) United States Patent
Min et al.

(10) Patent No.: US 12,753,151 B2
(45) Date of Patent: Oct. 6, 2026

(54) METHOD FOR PREPARING ISOCYANATE COMPOUND

(71) Applicant: Hanwha Solutions Corporation, Seoul (KR)

(72) Inventors: Ju Won Min, Daejeon (KR); Hyun Cheol Ryu, Daejeon (KR)

(73) Assignee: HANWHA SOLUTIONS CORPORATION, Seoul (KR)

( * ) Notice: Subject to any disclaimer, the term of this patent is extended or adjusted under 35 U.S.C. 154(b) by 620 days.

(21) Appl. No.: 18/259,824

(22) PCT Filed: Dec. 30, 2021

(86) PCT No.: PCT/KR2021/020328
§ 371 (c)(1),
(2) Date: Jun. 29, 2023

(87) PCT Pub. No.: WO2022/146090
PCT Pub. Date: Jul. 7, 2022

(65) Prior Publication Data

US 2024/0317679 A1 Sep. 26, 2024

(30) Foreign Application Priority Data

Dec. 30, 2020 (KR) ........................ 10-2020-0187830

(51) Int. Cl.
*C07C 263/10* (2006.01)

(52) U.S. Cl.
CPC .................................. *C07C 263/10* (2013.01)

(58) Field of Classification Search
CPC ... C07C 263/10; C07C 263/20; C07C 263/16; C07C 265/14
See application file for complete search history.

(56) References Cited

U.S. PATENT DOCUMENTS

| | | | |
|---|---|---|---|
| 2017/0101367 | A1 | 4/2017 | Knauf |
| 2021/0380528 | A1 | 12/2021 | Takamatsu |

FOREIGN PATENT DOCUMENTS

| | | | | |
|---|---|---|---|---|
| CN | 101671274 A | 3/2010 | | |
| CN | 101671276 A | 3/2010 | | |
| CN | 104203910 A | 12/2014 | | |
| CN | 109153637 A | 1/2019 | | |
| CN | 112154137 A | 12/2020 | | |
| JP | 2008174549 A | 7/2008 | | |
| JP | 2010-516640 A | 5/2010 | | |
| JP | 2018529694 A | 10/2018 | * | ........... C07C 263/10 |
| JP | 2018177811 A | 11/2018 | | |
| KR | 1019970001071 B1 | 3/1994 | | |
| KR | 20050089051 A | 9/2005 | | |

(Continued)

OTHER PUBLICATIONS

International Search Report dated Apr. 12, 2022.

*Primary Examiner* — Deborah D Carr
(74) *Attorney, Agent, or Firm* — Harvest IP Law, LLP

(57) ABSTRACT

The present invention relates to a method for preparing an isocyanate compound. According to the present invention, provided is a method for preparing an isocyanate compound that can recover and reuse materials used in the reaction during the preparation of an isocyanate compound using phosgene, and can minimize thermal denaturation of a reaction product and formation of by-products.

11 Claims, 2 Drawing Sheets

(56) References Cited

FOREIGN PATENT DOCUMENTS

| | | | | |
|---|---|---|---|---|
| KR | 20080033495 | A | 4/2008 | |
| KR | 20100087109 | A | 8/2010 | |
| KR | 20120038435 | A | 4/2012 | |
| KR | 20160138410 | A | 12/2016 | |
| KR | 20190142642 | A | 12/2019 | |
| WO | 2018-079502 | A1 | 5/2018 | |
| WO | WO-2019245192 | A1 * | 12/2019 | ........... C07C 263/20 |

* cited by examiner

【FIG.1】
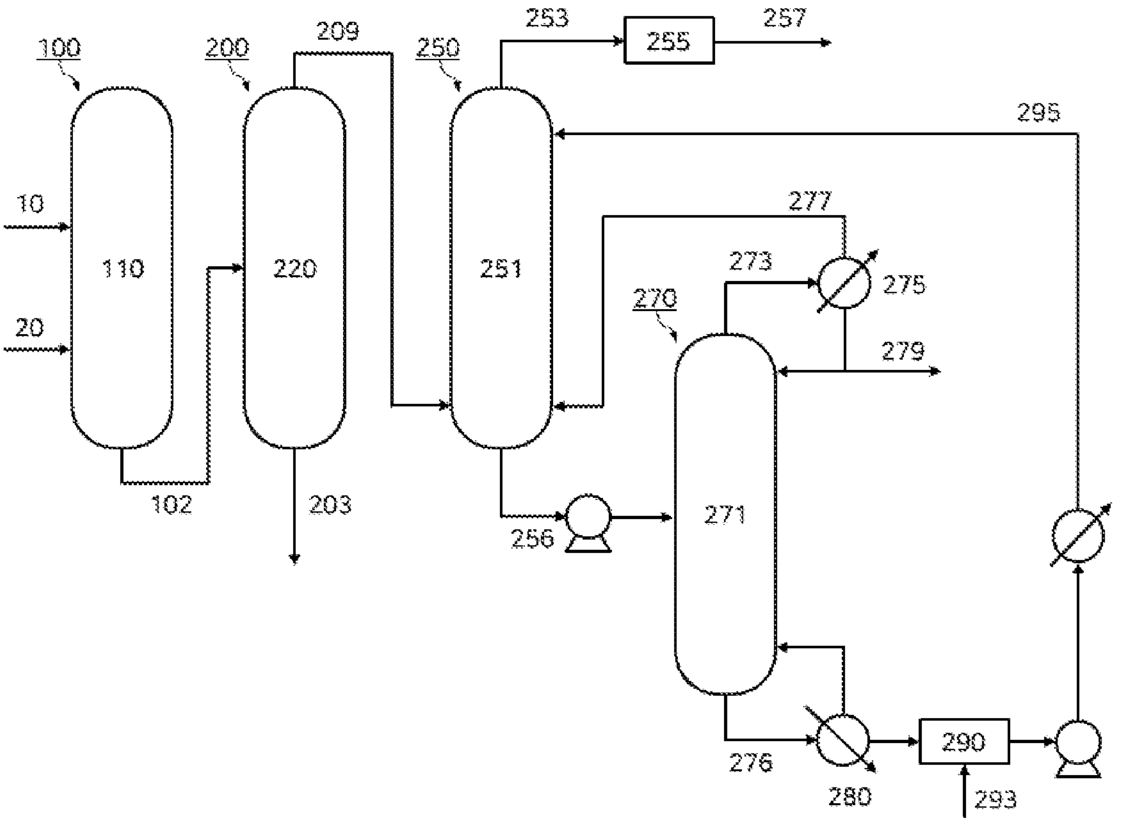

【FIG.2】
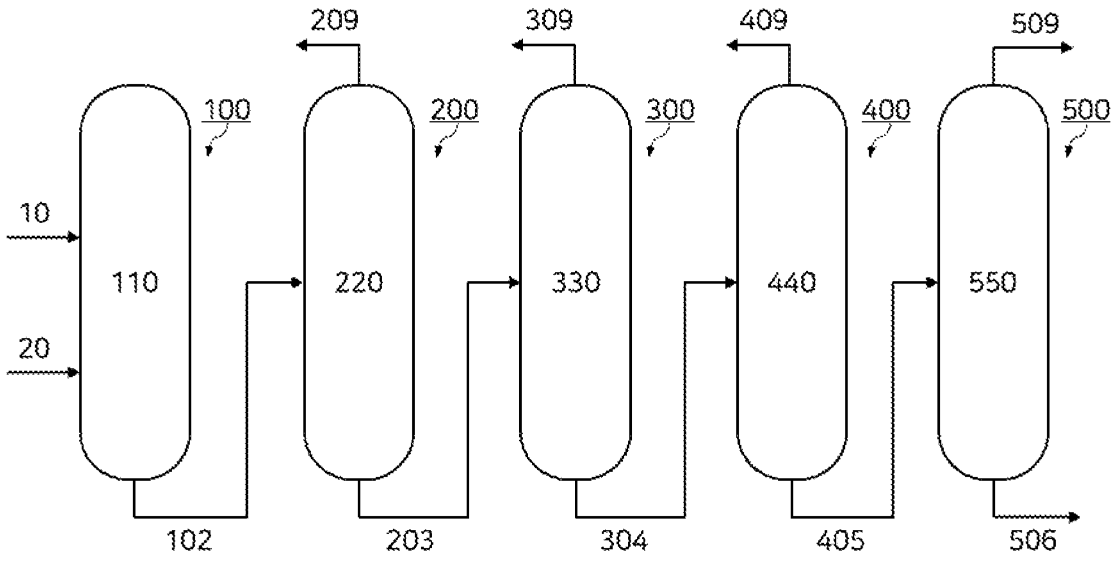

METHOD FOR PREPARING ISOCYANATE COMPOUND

CROSS REFERENCE TO RELATED APPLICATION(S)

This application is a National Stage of International Application No. PCT/KR2021/020328 filed on Dec. 30, 2021, claiming priority based on Korean Patent Application No. 10-2020-0187830 filed Dec. 30, 2020, the disclosures of which are incorporated herein by reference in their entireties.

TECHNICAL FIELD

The present invention relates to a method for preparing an isocyanate compound.

BACKGROUND ART

Although xylylene diisocyanate (hereinafter, referred to as XDI) contains an aromatic ring in its molecule, it is classified into aliphatic isocyanate. XDI is a compound very useful for raw materials such as polyurethane-based materials, polyurea-based materials, or polyisocyanurate-based materials in the fields of chemical industry, resin industry, and paint industry.

Commonly, when synthesizing isocyanate compound, many side reactions are generated, and thus, it is prepared by a method of reacting with anhydrous hydrochloric acid or carbonic acid to form a salt of amine compound and reacting it with phosgene.

As an example, XDI is prepared by reacting xylylene diamine (hereinafter referred to as XDA) with anhydrous hydrochloric acid to form an amine-hydrochloride salt, and then reacting it with phosgene. More specifically, in the prior art, an isocyanate compound such as XDI was prepared by reacting a liquid raw amine, such as XDA-containing solution, with anhydrous hydrochloric acid to form XDA-HCl hydrochloride, heating it to a high temperature of at least 100 °C or more, and then charging gas phase phosgene to progress a gas-liquid reaction.

The reaction of forming the isocyanate compound is a representative endothermic reaction, continuous heating and maintenance of a high temperature are required during the reaction so as to increase the yield.

By the way, since isocyanate compound such as XDI generally has high reactivity of the amino group, many side reactions are generated during the phosgenation reaction, and the by-products formed through the side reactions have an influence on a process in which isocyanate compounds are applied as raw materials (for example, a process for producing a polyurethane resin), thereby causing deterioration in resin quality.

As explained above, due the need to maintain a high temperature during the preparation process of isocyanate compound, and the high reactivity of the prepared isocyanate compound, such as XDI, there is a growing concern about the formation of by-products or the occurrence of side reactions by the thermal denaturation of products, and thus, high load has been frequently generated even in the purification process.

Due to such problems, various attempts have been made in the past to suppress side reactions or by-product generations during the preparation of isocyanate compound, but effective technology has not yet been developed.

In addition, attempts have been made to recover and reuse compounds such as phosgene and hydrogen chloride from exhaust gas generated during the preparation process of isocyanate compound, but there is a limit in that the efficiency is lowered.

DETAILED DESCRIPTION OF THE INVENTION

Technical Problem

It is an object of the present invention to provide a method for preparing an isocyanate compound that can recover and reuse materials used in the reaction during the preparation of an isocyanate compound using phosgene, and can minimize thermal denaturation of a reaction product and formation of by-products.

Technical Solution

According to one embodiment of the present invention, there is provided a method for preparing isocyanate compound, comprising:

a reaction step of reacting a salt of amine compound with phosgene in the presence of a solvent to obtain a reaction product containing an isocyanate compound, a degassing step of removing a gas phase from the reaction product, a scrubbing step of contacting the gas phase obtained in the degassing step with a cleaning solvent having a temperature of −15 °C to 0 °C under a negative pressure of 700 torr or more and less than 760 torr to obtain a phosgene-containing solution, and a distillation step of distilling the phosgene-containing solution under normal pressure to separate the phosgene contained in the phosgene-containing solution and the cleaning solvent, wherein the phosgene obtained in the distillation step is supplied to the reaction step, and wherein the cleaning solvent obtained in the distillation step is supplied to the scrubbing step.

Now, a method for preparing an isocyanate compound according to one embodiment of the present invention will be described.

Unless defined otherwise, all technical and scientific terms used herein have the same meaning as commonly understood by one of ordinary skill in the art to which this invention belongs. The terms used herein are for the purpose of describing specific embodiments only and is not intended to limit the scope of the invention.

The singular forms "a," "an" and "the" used herein are intended to include plural forms, unless the context clearly indicates otherwise.

It should be understood that the terms "comprise," "include", "have", etc. are used herein to specify the presence of stated feature, region, integer, step, action, element and/or component, but do not preclude the presence or addition of one or more other feature, region, integer, step, action, element, component and/or group.

While the present invention can be modified in various ways and take on various alternative forms, specific embodiments thereof are illustrated and described in detail below. However, it should be understood that there is no intent to limit the present invention to the particular forms disclosed, but on the contrary, the present invention covers all modifications, equivalents, and alternatives falling within the spirit and scope of the present invention.

In describing a position relationship, for example, when the position relationship is described as 'upon~', 'above~', 'below~', and 'next to~', one or more portions may be arranged between two other portions unless 'just' or 'direct' is used.

In describing a time relationship, for example, when the temporal order is described as 'after~', 'subsequent~', 'next~', and 'before~', a case which is not continuous may be included unless 'just' or 'direct' is used.

As used herein, the term "low boiling material" means a material having a boiling point lower than that of the isocyanate compound which is a target product according to the present invention, and the term "high boiling material" means a material having a boiling point higher than that of the isocyanate compound, which is a target product according to the present invention.

As used herein, the term "bottom" of the distillation column means an outlet through which the lower discharged products of the distillation column are discharged to the outside of the distillation column, the term "top" of the distillation column means an outlet through which the upper discharged products of the distillation column are discharged to the outside of the distillation column.

According to one embodiment of the present invention, there is provided a method for preparing isocyanate compound, comprising:

- a reaction step of reacting a salt of amine compound with phosgene in the presence of a solvent to obtain a reaction product containing an isocyanate compound,
- a degassing step of removing a gas phase from the reaction product,
- a scrubbing step of contacting the gas phase obtained in the degassing step with a cleaning solvent having a temperature of −15 °C to 0 °C under a negative pressure of 700 torr or more and less than 760 torr to obtain a phosgene-containing solution, and
- a distillation step of distilling the phosgene-containing solution under normal pressure to separate the phosgene contained in the phosgene-containing solution and the cleaning solvent,
- wherein the phosgene obtained in the distillation step is supplied to the reaction step, and
- wherein the cleaning solvent obtained in the distillation step is supplied to the scrubbing step.

According to another embodiment of the present invention, there is provided a method for preparing isocyanate compound, further comprising:

- a desolvation step of removing a solvent from the reaction product from which the gas phase obtained in the degassing step has been removed,
- a low boiling material-removing step of removing low boiling materials (i.e., lights) from the reaction product from which the solvent has been removed, and
- a high boiling material-removing step of removing high boiling materials (i.e., heavies) from the reaction product from which the low boiling materials have been removed.

During the preparation of an isocyanate compound using phosgene, exhaust gases containing phosgene, hydrogen chloride and the like are discharged during the main reaction and purification processes. In accordance with environmental regulations, the exhaust gases are discharged into the atmosphere after removal of harmful substances by post-treatment.

The present inventors have found, as a result of continuous research, that when the exhaust gases from all processes including the gas phase obtained in the degassing step are processed through the scrubbing step and the distillation step under the above conditions, phosgene, hydrogen chloride and the like contained in the exhaust gases can be more effectively recovered, and the recovered compounds can be supplied to the steps in need thereof, thereby reducing costs and increasing process efficiencies.

Furthermore, inventors have found that the reaction step, the degassing step, the desolvation step, the low boiling material-removing step, and the high boiling material-removing step are progressed to prepare an isocyanate compound, especially when the above steps are progressed under the above temperature and pressure conditions, the thermal denaturation of a reaction product and the formation of by-products can be minimized, and a high-purity isocyanate compound can be obtained.

FIG. 1 schematically shows the process and apparatus utilized in the method for preparing an isocyanate compound according to an embodiment of the present invention. Each step that can be included in the method for preparing an isocyanate compound according to an embodiment of the invention will be described below with reference to FIG. 1.

(Reaction Step)

First, a reaction step is progressed in which a salt of amine compound and phosgene are reacted in the presence of a solvent to obtain a reaction product containing an isocyanate compound, the solvent, and unreacted phosgene.

According to one embodiment of the invention, the amine compound is preferably applied as a salt of the amine compound in order to suppress rapid reactions and side reactions between the amine compound and phosgene. For example, the salt of amine compound may be a hydrochloride or carbonic acid salt of the amine compound.

The salt of the amine compound may be prepared by reacting an amine compound with anhydrous hydrochloric acid or carbonic acid and performing a neutralization reaction. The neutralization reaction can be progressed at a temperature of 20 to 80 °C.

The supply ratio of the anhydrous hydrochloric acid or carbonic acid may be, for example, 2 to 10 moles, 2 to 6 moles, or 2 to 4 moles, based on 1 mole of the amine compound.

Preferably, the amine compound may be a fatty amine having an aliphatic group in its molecule. Specifically, the aliphatic amine may be a chained or cyclic aliphatic amine. More specifically, the aliphatic amine may be a bifunctional or higher chained or cyclic aliphatic amine containing at least two amino groups in its molecule.

For example, the amine compound may be at least one compound selected from the group consisting of hexamethylenediamine, 2,2-dimethylpentanediamine, 2,2,4-trimethylhexanediamine, butenediamine, 1,3-butadiene-1,4-diamine, 2,4,4-trimethylhexamethylenediamine, 1,6,11-undecatriamine, 1,3,6-hexamethylenetriamine, 1,8-diisocyanato-4-(isocyanatomethyl)octane, bis(aminoethyl) carbonate, bis(aminoethyl)ether, xylylenediamine, α,α,α',α'-tetramethylxylylenediamine, bis(aminoethyl)phthalate, bis(aminomethyl)cyclohexane, dicyclohexylmethanediamine, cyclohexanediamine, methylcyclohexanediamine, dicyclohexyldimethylmethanediamine, 2,2-dimethyldicyclohexylmethanediamine, 2,5-bis(aminomethyl)bicyclo-[2,2,1]-heptane, 2,6-bis(aminomethyl)bicyclo-[2,2,1]-heptane, 3,8-bis(aminomethyl)tricyclodecane, 3,9-bis(aminomethyl) tricyclodecane, 4,8-bis(aminomethyl)tricyclodecane, 4,9-bis (aminomethyl)tricyclodecane, bis(aminomethyl)norbornene, and xylylenediamine.

Further, the amine compound may be at least one sulfur-containing aliphatic amine selected from the group consisting of bis(aminomethyl)sulfide, bis(aminoethyl)sulfide, bis (aminopropyl)sulfide, bis(aminohexyl)sulfide, bis (aminomethyl)sulfone, bis(aminomethyl)disulfide, bis (aminoethyl)disulfide, bis(aminopropyl)disulfide, bis (aminomethylthio)methane, bis(aminoethylthio)methane, bis(aminoethylthio)ethane, bis(aminomethylthio)ethane, and 1,5-diamino-2-aminomethyl-3-thiapentane.

Among the above amine compounds, xylylenediamine (XDA) can exhibit superior effects when applied to the method for preparing an isocyanate compound according to one embodiment of the invention. Preferably, the amine compound may be at least one compound selected from the group consisting of m-xylylenediamine, p-xylylenediamine and o-xylylenediamine.

According to an embodiment of the invention, the reaction step is progressed in a gas-liquid-solid three-phase reaction in which a salt of solid-phase amine compound and gas phase phosgene are reacted in the presence of a solvent. Accordingly, rapid reactions can be effectively suppressed, and side reactions and formation of by-products can be minimized.

When the salt of amine compound and phosgene are reacted in the presence of a solvent, phosgene may be charged at a time, or may be charged dividedly. For example, a small amount of phosgene can be primarily charged at a relatively low temperature, and reacted with the salt of amine compound to produce the intermediate. Subsequently, the remaining amount of phosgene can be secondarily charged at a relatively high temperature, and reacted with the intermediate to obtain a reaction solution containing an isocyanate compound. As an example, xylylene diamine and a small amount of phosgene are reacted to produce an intermediate in the form of a carbamoyl salt, to which the remaining amount of phosgene is then charged, and the intermediate in the form of a carbamoyl salt can be reacted with phosgene to form an aliphatic isocyanate such as xylylene diisocyanate.

Through such reaction steps, a time during which the final product isocyanate compound is exposed to high temperature can be minimized. Furthermore, the intermediate is formed at a relatively low temperature, thereby reducing a time during which a high temperature should be maintained in the whole reaction process. In addition, the amount of heat charged to the whole process can be reduced. Further, the high-temperature reaction time of phosgene can be relatively shortened, and the risk of explosive vaporization of phosgene can also be reduced.

The reaction step is progressed in the presence of a solvent containing at least one of an aromatic hydrocarbon-based solvent and an ester-based solvent. The solvent may be selected in consideration of the temperature at which the reaction step is progressed.

The aromatic hydrocarbon-based solvent may be a halogenated aromatic hydrocarbon-based solvent such as monochlorobenzene, 1,2-dichlorobenzene and 1,2,4-trichlorobenzene.

The ester-based solvent may be fatty acid esters such as amyl formate, n-butyl acetate, isobutyl acetate, n-amyl acetate, isoamyl acetate, methylisoamyl acetate, methoxybutyl acetate, sec-hexyl acetate, 2-ethylbutyl acetate, 2-ethylhexyl acetate, cyclohexyl acetate, methylcyclohexyl acetate, benzyl acetate, ethyl propionate, n-butyl propionate, isoamyl propionate, ethyl acetate, butyl stearate, butyl lactate, and amyl lactate; or aromatic carboxylic acid esters such as methyl salicylate, dimethyl phthalate and methyl benzoate.

According to one embodiment of the invention, the salt of amine compound in the reaction step may be contained in the solvent at a concentration of 20% by volume or less, for example, 1 to 20% by volume, or 5 to 20% by volume. When the concentration of the salt of amine compound contained in the solvent exceeds 20% by volume, a large amount of salt is likely to precipitate in the reaction step.

The reaction step may be progressed at a temperature of 165 °C or less, preferably 80 °C to 165 °C.

According to one embodiment of the invention, when phosgene is dividedly charged in the reaction step, it can be charged in an amount of 10 to 30% by weight, or 12 to 30% by weight, or 15 to 28% by weight based on the entire amount of phosgene charged at a temperature of 80 °C to 100 °C or 85 °C to 95 °C. Under such reaction conditions, rapid reactions are suppressed and an intermediate in the form of a carbamoyl-based salt can be selectively and effectively formed. Subsequently, while charging the remaining amount of phosgene at a temperature of 110 °C to 165 °C or 120 °C to 150 °C, the intermediate and the phosgene can be reacted to obtain a reaction product containing an isocyanate compound.

The isocyanate compound may vary depending on the type of the amine compound used in the reaction step. For example, the isocyanate compound may be at least one compound selected from the group consisting of n-pentyl isocyanate, 6-methyl-2-heptane isocyanate, cyclopentyl isocyanate, hexamethylene diisocyanate (HDI), isophorone diisocyanate (IPDI), diisocyanatomethylcyclohexane (H6TDI), xylylene diisocyanate (XDI), diisocyanatocyclohexane (t-CHDI) and di(isocyanatocyclohexyl)methane (H12MDI).

In particular, the method for preparing an isocyanate compound according to an embodiment of the invention may be further useful for the preparation of xylylene diisocyanate (XDI). XDI includes 1,2-XDI (o-XDI), 1,3-XDI (m-XDI), and 1,4-XDI (p-XDI) as structural isomers.

The reaction step can be progressed either batchwise or continuously. The reaction step can be progressed in a reaction unit 100 that includes a reactor 110 having a rotating shaft; an amine compound salt supply line 10 and a phosgene supply line 20 that supply reactants to the inside of the reactor; a heat source that supplies a heat quantity to the reactor; and a reaction product transfer line 102 that transfers the reaction product obtained in the reactor to a subsequent purification step.

(Degassing Step)

Then, a degassing step of removing the gas phase from the reaction product is progressed.

In the degassing step, a gas phase such as surplus phosgene or byproduct hydrogen chloride is removed from the reaction product by a known degassing unit 200.

A method of removing the gas phase from the reaction product may include a method of supplying and aerating gas, or a method of separating the gas phase from the reaction product using a flash tank or a distillation column.

In particular, according to an embodiment of the invention, in order to minimize the formation of by-products in the degassing step, the degassing step is preferably progressed at a temperature of 145 °C to 165 °C and a pressure of 100 torr to 600 torr.

In one example, the degassing step may be progressed in a distillation column, wherein setting the temperature at the bottom of the distillation column to 145 °C to 165 °C and operating the distillation column under a column top pressure of 100 torr to 600 torr may be advantageous to minimize the formation of by-products. Here, the temperature at the bottom of the distillation column may mean the temperature of a reboiler connected to the bottom of the distillation column. And, the pressure at the top of the distillation column may mean the pressure of a condenser connected to the top of the distillation column.

Preferably, the temperature at which the degassing step is progressed may be 145 °C to 165 °C, or 150 °C to 165 °C, or 150 °C to 160 °C, or 155 °C to 160 °C. And, preferably, the pressure at which the degassing step is progressed may be 100 torr to 600 torr, or 200 torr to 500 torr, or 300 torr to 450 torr, or 350 torr to 450 torr.

When the temperature and pressure at which the degassing step is progressed do not satisfy the above ranges, the formation of by-products in the degassing step can increase, and the removal efficiency of a gas phase can decrease, whereby the concentration of the isocyanate compound in the reaction product obtained from the degassing step can decrease.

As an example, the degassing step can be progressed in a degassing unit 200 including a distillation column 220 configured so as to be able to remove a gas phase from the reaction product supplied via the reaction product transfer line 102 of the reaction unit 100; a gas phase discharge line 209 that discharges a gas phase to the top of the distillation column; and a reaction product transfer line 203 that discharges the reaction product from which the gas phase has been removed to the bottom of the distillation column and transfers it to a subsequent step.

(Scrubbing Step)

Then, a scrubbing step is progressed in which the gas phase obtained in the degassing step is brought into contact with a cleaning solvent having a temperature of −15 °C to 0 °C under a negative pressure of 700 torr or more and less than 760 torr to obtain a phosgene-containing solution.

In the scrubbing step, phosgene is recovered by a known scrubbing unit 250 from the gas phase obtained in the degassing step.

A method of recovering phosgene from the gas phase may include a method of supplying the gas phase to the scrubbing tower 251 and bringing it into contact with a cleaning solvent.

The type of the scrubbing tower 251 may be determined in consideration of contact efficiency between the gas phase supplied from the gas phase discharge line 209 and the cleaning solvent supplied from the solvent supply line 295, and the like. As a non-limiting example, the scrubbing tower 251 is a packed column type scrubbing tower, or a multi-stage tray type scrubbing tower. The packed column type scrubbing tower may have a packing material such as lashing ring, pall ring, saddle, gauze, or structured packing applied inside.

Considering the efficiency of the scrubbing step, the gas phase may be supplied from the lower part of the scrubbing tower 251, and the cleaning solvent may be supplied from the upper part of the scrubbing tower 251.

The cleaning solvent may be an organic solvent capable of scrubbing phosgene contained in the gas phase. As an example, the cleaning solvent may be at least one solvent selected from the group consisting of ethylene dichloride, monochlorobenzene, 1,2-dichlorobenzene, and 1,2,4-trichlorobenzene.

In particular, considering the scrubbing efficiency of phosgene, the scrubbing step is preferably progressed under negative pressure. More preferably, the scrubbing step may be progressed under a negative pressure of 700 torr or more and less than 760 torr, or 710 torr to 750 torr, or 720 torr to 740 torr.

And, considering the scrubbing efficiency of phosgene, the cleaning solvent applied in the scrubbing step preferably has a temperature of −15 °C to 0 °C, or −12 °C to −3 °C, or −10 °C to −5 °C.

If the temperature of the cleaning solvent is too low, the cleaning solvent may freeze, which may reduce the scrubbing efficiency. However, if the temperature of the cleaning solvent is too high, the amount of the cleaning solvent contained in the top stream of the scrubbing tower 251 increases, which may make it difficult to remove the cleaning solvent by a filter 255.

In the scrubbing step, a solution in which phosgene is dissolved in the cleaning solvent (hereinafter referred to as 'phosgene-containing solution') is discharged to the bottom of the scrubbing tower 251 through a bottom stream line 256. A non-condensable gas (for example, hydrochloric acid gas or carbonic acid gas) from which phosgene has been degassed is discharged to the upper part of the scrubbing tower 251 through a column top stream line 253.

The non-condensable gas discharged through the column top stream line 253 is recovered outside the reaction system via a filter 255 for removing residual cleaning solvent and then via a non-condensable gas discharge line 257. Here, as the filter 255, a filter capable of removing residual cleaning solvent contained in the non-condensable gas, such as an activated carbon filter, can be applied. The non-condensable gas recovered via the non-condensable gas discharge line 257 can be used for a reaction to form a salt of the amine compound in the reaction step.

The phosgene-containing solution discharged through the bottom stream line 256 is transferred to a distillation unit 270.

(Distillation Step)

Then, a distillation step is progressed in which the phosgene-containing solution obtained in the scrubbing step is distilled under normal pressure to separate phosgene contained in the phosgene-containing solution and the cleaning solvent.

In the distillation step, phosgene and the cleaning solvent are separated and recovered from the phosgene-containing solution by a distillation unit 270 including a known distillation column 271.

According to one embodiment of the invention, in order to secure distillation efficiency of the phosgene-containing solution, the distillation step is preferably progressed under normal pressure (e.g., 760 torr).

In the distillation step, phosgene separated from the phosgene-containing solution is discharged to the upper part of the distillation column 271 through a column top stream line 273. The discharged phosgene is supplied to a condenser 275. Part of the phosgene condensed in the condenser 275 is re-supplied to the distillation column 271, and the remainder is recovered through a phosgene discharge line 279. The gas phase that is not condensed in the condenser 275 is supplied to the bottom of the scrubbing tower 251 of the scrubbing unit 250 through a gas phase discharge line 277. The phosgene recovered via the phosgene discharge line 279 is used as a reactant in the reaction step. That is, the phosgene recovered via the phosgene discharge line 279 in the distillation step is supplied to the reactor 110 through the phosgene supply line 20 of the reaction unit 100.

In the distillation step, the cleaning solvent-containing solution separated from the phosgene-containing solution is discharged to the bottom of the distillation column 271 through a bottom stream line 276. The discharged cleaning solvent-containing solution is supplied to a reboiler 280. The low boiling fraction in the reboiler 280 is re-supplied to the bottom of the distillation column 271, and the cleaning solvent, which is the remaining fraction, is transferred to a solvent recovery drum 290.

In addition to the cleaning solvent transported from the reboiler 280, a fresh cleaning solvent necessary for progressing the distillation step is further supplied to the solvent recovery drum 290. The fresh cleaning solvent is supplied to the solvent recovery drum 290 through a solvent supply line 293. The cleaning solvent collected in the solvent recovery drum 290 is supplied to the upper part of the scrubbing tower 251 of the scrubbing unit 250 through a solvent supply line 295. At this time, the cleaning solvent is supplied to the scrubbing tower 251 via a heat exchanger that lowers the temperature of the cleaning solvent to 0 °C or less. Preferably, the cleaning solvent is supplied to the scrubbing tower 251 at a temperature of −15 °C to 0 °C, or −12 °C to −3 °C, or −10 °C to −5 °C.

Meanwhile, according to another embodiment of the invention, the method for preparing an isocyanate compound may further comprise a desolvation step of removing a solvent from the reaction product from which the gas phase obtained in the degassing step has been removed, a low boiling material-removing step of removing low boiling materials (i.e., lights) from the reaction product from which the solvent has been removed, and a high boiling material-removing step of removing high boiling materials (i.e., heavies) from the reaction product from which the low boiling materials have been removed.

FIG. 2 schematically shows the process and apparatus used in the method for preparing an isocyanate compound according to the embodiment. Steps that can be further included in the method for preparing an isocyanate compound according to the embodiment will be described below with reference to FIG. 2.

(Desolvation Step)

Then, a desolvation step may be progressed in which a solvent is removed from the reaction product from which the gas phase has been removed.

In the desolvation step, the solvent is distilled off from the reaction product from which the gas phase has been removed by a known desolvation unit 300.

According to one embodiment of the invention, in order to minimize thermal denaturation of the reaction product and formation of by-products in the desolvation step, the desolvation step is preferably progressed at a temperature of 100 °C to 165 °C and a pressure of 30 torr or less.

In one example, the desolvation step can be progressed in a distillation column, wherein setting the temperature at the bottom of the distillation column to 100 °C to 165 °C and operating the distillation column under a column top pressure of 30 torr or less can be advantageous to minimize the thermal degradation and the formation of by-products. Here, the temperature at the bottom of the distillation column may mean the temperature of a reboiler connected to the bottom of the distillation column. And, the pressure at the top of the distillation column may mean the pressure of a condenser connected to the top of the distillation column.

Preferably, the temperature at which the desolvation step is progressed may be 100 °C to 165 °C, or 115 °C to 165 °C, or 115 °C to 160 °C, or 130 °C to 160 °C. And, preferably, the pressure at which the desolvation step is progressed may be 5 torr to 30 torr, or 5 torr to 25 torr, or 10 torr to 20 torr, or 10 torr to 15 torr.

When the temperature and pressure at which the desolvation step is progressed do not satisfy the above ranges, the thermal denaturation and the formation of by-products in the solvent removal step may increase, and the solvent removal efficiency may decrease, whereby the concentration of the isocyanate compound in the reaction product obtained from the desolvation step may decrease.

In one example, the desolvation step can be progressed in a desolvation unit 300 that includes a distillation column 330 configured so as to be able to remove a solvent from the reaction product supplied via the reaction product transfer line 203 of the degassing unit 200; a solvent discharge line 309 that discharges a solvent to the top of the distillation column; and a reaction product transfer line 304 that discharges the reaction product from which the solvent has been removed to the bottom of the distillation column, and transfers it to a subsequent step.

In order to minimize the high temperature residence time of the reaction product in the desolvation step, a distillation column 440 equipped with apparatuses such as a kettle type reboiler, a thin-film evaporator, a force circulated reboiler, and a jacketed vessel type reboiler can be utilized.

(Low Boiling Material-Removing Step)

Then, a low boiling material-removing step may be progressed in which low boiling materials (i.e., lights) are removed from the reaction product from which the solvent obtained in the desolvation step has been removed.

In the low boiling material-removing step, the low boiling materials (lights) are removed by a known low boiling material-removing unit 400 from the reaction product from which the solvent has been removed.

The low boiling material means a material having a boiling point lower than that of the isocyanate compound, which is the main product in the reaction step. Examples of the low boiling materials include materials produced by side reactions in the process of obtaining the main product. As an example, in the process of preparing XDI as the isocyanate compound, the low boiling material may include monoisocyanate such as (chloromethyl)benzyl isocyanate (CBI) and ethylphenyl isocyanate (EBI).

According to one embodiment of the invention, in order to minimize the thermal denaturation of reaction products and the formation of by-products in the low boiling material-removing step, the low boiling material-removing step is preferably progressed under the conditions where the temperature at the bottom of the distillation column 440 is set to 150 °C to 165 °C and the pressure at the top of the distillation column is set to 5 torr or less. Here, the temperature at the bottom of the distillation column may mean the temperature of a reboiler connected to the bottom of the distillation column.

Preferably, the temperature at which the low boiling material-removing step is progressed may be 150 °C to 165 °C, or 155 °C to 165 °C, or 155 °C to 162 °C, or 160 °C to 162 °C. And, preferably, the upper pressure at which the low boiling material-removing step is progressed may be 1 torr to 5 torr, or 2 torr to 5 torr, or 2 torr to 4 torr.

If the temperature and pressure at which the low boiling material-removing step is progressed do not satisfy the above ranges, the thermal denaturation and the formation of by-products in the low boiling material-removing step may increase, and the removal efficiency of low boiling materials may decrease, whereby the concentration of isocyanate compounds in the reaction product obtained from the low boiling material-removing step can be reduced.

In one example, the low boiling material-removing step can be progressed in a low boiling material-removing unit 400 that includes a distillation column 440 configured so as to be able to remove low boiling materials from the reaction product supplied through the reaction product transfer line 304 of the desolvation unit 300; a low boiling material discharge line 409 that discharges low boiling materials to the top of the distillation column; and a reaction product transfer line 405 that discharges the reaction product from which the low boiling materials have been removed to the bottom of the distillation column, and transfers it to a subsequent step.

In order to minimize the high temperature residence time of the reaction product in the low boiling material-removing step, a distillation column 440 equipped with apparatuses such as a kettle type reboiler, a thin-film evaporator, a force circulated reboiler, and a jacketed vessel type reboiler can be utilized.

(High Boiling Material-Removing Step)

Then, a high boiling material-removing step may be progressed in which high boiling materials (i.e., heavies) are removed from the reaction product from which the low boiling materials obtained in the low boiling material-removing step have been removed.

In the high boiling material-removing step, high boiling materials (i.e., heavies) are removed by a known high boiling material-removing unit 500 from the reaction product from which the low boiling materials have been removed.

The high boiling material means a material having a boiling point higher than that of the isocyanate compound, which is the main product in the reaction step. Examples of the high boiling materials include high-molecular-weight by-products such as oligomers or polymers including dimers, trimers or higher multimers of isocyanate compounds formed in the step of obtaining the main product.

According to one embodiment of the invention, in order to minimize the thermal denaturation of the reaction product and the formation of by-products in the high boiling material-removing step, the high boiling material-removing step may preferably be progressed at a temperature of 145 °C to 165 °C and a pressure of 1 torr or less.

In one example, the high boiling material-removing step may be progressed under a thin-film evaporator, wherein setting the temperature at the bottom of the distillation column to 145 °C to 165 °C and operating the distillation column under a column top pressure of 1 torr or less can be advantageous to minimize the thermal degradation and the formation of by-products.

Preferably, the temperature at which the high boiling material-removing step is progressed may be 145 °C to 165 °C, or 150 °C to 165 °C, or 150 °C to 160 °C, or 155 °C to 160 °C. And, preferably, the pressure at which the high boiling material-removing step is progressed may be 0.1 torr to 1 torr, or 0.5 torr to 1 torr.

If the temperature and pressure at which the high boiling material-removing step is progressed do not satisfy the above ranges, the thermal denaturation and the formation of by-products in the high boiling material-removing step may increase, and the removal efficiency of high boiling materials may decrease, whereby the concentration of the isocyanate compound obtained from the high boiling material-removing step may decrease.

In one example, the high boiling material-removing step may be progressed in a high boiling material-removing unit 500 that includes a thin-film evaporator 550 configured so as to be able to remove high boiling materials from the reaction product supplied through the reaction product transfer line 405 of the low boiling material-removing unit 400; an isocyanate compound discharge line 509 that discharges an isocyanate compound to a condensing section of the thin-film evaporator; and a high boiling material discharge line 506 that discharges the high boiling material to the bottom of the thin-film evaporator.

Advantageous Effects

According to the present invention, provided is a method for preparing an isocyanate compound that can recover and reuse materials used in the reaction during the preparation of an isocyanate compound using phosgene, and can minimize thermal denaturation of a reaction product and formation of by-products.

BRIEF DESCRIPTION OF THE DRAWINGS

FIGS. 1 and 2 schematically show the process and apparatus used in the method for preparing an isocyanate compound according to embodiments of the invention.

DESCRIPTION OF REFERENCE NUMERALS

10: amine compound salt supply line
20: phosgene supply line
100: reaction unit
110: reactor
102: reaction product transfer line
200: degassing unit
220: distillation column
209: gas phase discharge line
203: reaction product transfer line
250: scrubbing unit
251: scrubbing tower
253: column top stream line
255: filter
257: non-condensable gas discharge line
256: bottom stream line
270: distillation unit
271: distillation column
273: column top stream line
275: condenser
277: gas phase discharge line
279 phosgene discharge line
276: bottom stream line
280: reboiler
290: solvent recovery drum
293 solvent supply line
295 solvent supply line
300: desolvation unit
330: distillation column
309 solvent discharge line
304 reaction product transfer line
400: low boiling material-removing unit
440: distillation column
409: low boiling material discharge line
405: reaction product transfer line
500: high boiling material-removing unit
550: thin-film evaporator
506: high boiling material discharge line
509: isocyanate compound discharge line

DETAILED DESCRIPTION OF THE EMBODIMENTS

Hereinafter, the actions and effects of the invention will be explained in more detail through specific examples of the invention. However, these examples are presented only as the illustrations of the invention, and the scope of the right of the invention is not determined thereby.

Example 1

1,3-XDI (m-XDI) was prepared by the following process using the apparatus shown in FIGS. 1 and 2.

(Reaction Step)

Under normal temperature and pressure conditions, 500 kg of hydrochloric acid and 560 kg of m-xylylenediamine (m-XDA) were reacted in 6500 kg of 1,2-dichlorobenzene (o-DCB) solvent for 4 hours to form 870 kg of the hydrochloride salt of m-xylylenediamine.

870 kg of the hydrochloride salt of m-xylylenediamine was charged into a reactor 110 through a supply line 10, and the temperature of the reactor was raised to 125 °C. During the progress of the reaction, a total of 1359 kg of phosgene was put into the reactor through the supply line 20, and stirred. A dry ice-acetone condenser was used from the time of charging phosgene to the time of completion of the reaction to prevent phosgene from leaking to the outside. The reaction was allowed to progress for 1.5 hours at a temperature of 90 °C.

After that, the reactor was heated so that the internal temperature thereof was 125 °C, and 6000 kg of phosgene was further charged. The temperature of the reactor was maintained at 125 °C, and further stirred for 4.5 hours until the reaction solution became clear. Heating was stopped after the reaction solution became clear. The reaction product obtained by the above method was transferred to the degassing unit 200 through a transfer line 102.

(Degassing Step)

The distillation column 220 of the degassing unit 200 was configured so as to be able to remove the gas phase from the reaction product supplied through the transfer line 102.

Specifically, the distillation column 220 used was a packing tower packed with Mellapak, which is a type of structural packing, and had a height of about 6 m.

The temperature at the bottom of the distillation column 220 was set to 155 °C and the distillation column 220 was operated under a column top pressure of 400 torr.

About 150 kg/hr of the reflux stream was re-charged to a distillation column 220, which corresponds to a reflux ratio of about 3.2 relative to the column top outflow amount.

The gas phase containing phosgene was discharged through a gas phase discharge line 209 connected to the top of the distillation column 220. The gas phase discharged via the gas phase discharge line 209 was transferred to a scrubbing tower 251 of the scrubbing unit 250. The reaction product from which the gas phase has been removed was transferred to the desolvation unit 300 through the transfer line 203 connected to the bottom of the distillation column 220.

(Scrubbing Step)

The scrubbing tower 251 of the scrubbing unit 250 was configured so as to be able to recover phosgene from the gas phase supplied through the gas phase discharge line 209.

Specifically, the scrubbing tower 251 used was a packing tower packed with Mellapak, which is a kind of structural packing, and had a height of about 4 m.

The scrubbing tower 251 was operated under a negative pressure of 700 torr.

The gas phase was supplied to the lower part of the scrubbing tower 251. The cleaning solvent for scrubbing the phosgene contained in the gas phase was supplied to the upper part of the scrubbing tower 251 through a solvent supply line 295. As the cleaning solvent, 1,2-dichlorobenzene (o-DCB) having a temperature of −15 °C was used.

A solution in which phosgene was dissolved in the cleaning solvent (hereinafter referred to as a 'phosgene-containing solution') was discharged to the lower part of the scrubbing tower 251 through a bottom stream line 256. A non-condensable gas (hydrochloric acid gas) degassed with phosgene was discharged to the upper part of the scrubbing tower 251 through a column top stream line 253.

The hydrochloric acid gas discharged through the column top stream line 253 was recovered through the discharge line 257 via the activated carbon filter 255 for removing residual solvent. The recovered hydrochloric acid gas was supplied to a reaction for forming a salt of the amine compound in the reaction step.

The phosgene-containing solution discharged through the bottoms stream line 256 was transferred to the distillation unit 270.

(Distillation Step)

The distillation column 271 of the distillation unit 270 was configured to separate phosgene and the cleaning solvent from the phosgene-containing solution supplied through the bottom stream line 256 of the scrubbing unit 250.

Specifically, the distillation column 271 is an about 5 m column composed of 7 stages of bubble cap trays. About 400 kg/hr of the reflux stream was re-charged to the distillation column 271, which corresponds to a reflux ratio of about 1.4 relative to the column top outflow amount.

The temperature at the bottom of the distillation column 271 was set to 181 °C, and the distillation column 271 was operated under a column top pressure of 760 torr.

Phosgene separated from the phosgene-containing solution was discharged to the upper part of the distillation column 271 through a column top stream line 273. The discharged phosgene was supplied to a condenser 275. Part of the phosgene condensed in the condenser 275 was re-supplied to the distillation column 271, and the remainder was recovered via a discharge line 279. The recovered phosgene was supplied to the reactor 110 through the phosgene supply line 20 of the reaction unit 100. The gas phase not condensed in the condenser 275 was supplied to the bottom of the scrubbing tower 251 of the scrubbing unit 250 through a discharge line 277.

The solution containing the cleaning solvent was discharged to the bottom of the distillation tower 271 through the bottom stream line 276. The discharged cleaning solvent-containing solution was supplied to a reboiler 280. The low boiling fraction in the reboiler 280 was re-supplied to the bottom of the distillation column 271, and the cleaning solvent, which is the remaining fraction, was transferred to the solvent recovery drum 290.

A fresh cleaning solvent was further supplied to the solvent recovery drum 290 through a solvent supply line 293. The cleaning solvent collected in the solvent recovery drum 290 was supplied to the upper part of the scrubbing tower 251 of the scrubbing unit 250 through the solvent supply line 295. The washing solvent was supplied to the scrubbing tower 251 in a state where it was cooled to a temperature of −15 °C in a heat exchanger.

(Desolvation Step)

The distillation column 330 of the desolvation unit 300 was configured so as to be able to remove the solvent from the reaction product supplied through the transfer line 203.

Specifically, the distillation column 330 used was a packing tower packed with Mellapak, which is a type of structural packing, and had a height of about 7 m.

The temperature at the bottom of the distillation column 330 was set to 160 °C, and the distillation column 330 was operated under a column top pressure of 15 torr.

About 600 kg/hr of the reflux stream was re-charged to the distillation column 330, which corresponds to a reflux ratio of about 0.5 relative to the column top outflow amount.

A solvent including 1,2-dichlorobenzene (o-DCB) was discharged through a solvent discharge line 309 connected to the top of the distillation column 330. The reaction product from which the solvent has been removed was transferred to the degassing unit 400 through the transfer line 304 connected to the bottom of the distillation column 330.

(Low Boiling Material-Removing Step)

The distillation column 440 of the high boiling material-removing unit 400 was configured so as to be able to remove low boiling materials from the reaction product supplied through the transfer line 304.

Specifically, the distillation column 440 used was a packing tower packed with Mellapak, which is a type of structural packing, and had a height of about 13 m.

The temperature at the bottom of the distillation column 440 was set to 160 °C, and the distillation column 440 was operated under a column top pressure of 3 torr.

About 40 kg/hr of the reflux stream was re-charged to the distillation column 440, which corresponds to a reflux ratio of about 2.0 relative to the column top outflow amount.

Low boiling materials including (chloromethyl)benzyl isocyanate (CBI) were discharged through the low boiling material discharge line 409 connected to the top of the distillation column 440. The reaction product from which the low boiling materials were removed was transferred to the high boiling material-removing unit 500 through a transfer line 405 connected to the bottom of the distillation column 440.

(High Boiling Material-Removing Step)

The thin-film evaporator 550 of the high boiling material-removing unit 500 was configured so as to be able to remove high boiling materials from the reaction product supplied through the transfer line 405.

Specifically, the thin-film evaporator 550 used was an evaporator in the form of a short path evaporator having a condenser installed therein.

The bottom temperature of the thin-film evaporator 550 was set to 160 °C, and the thin-film evaporator 550 was operated under an evaporator bottom pressure of 0.5 torr.

About 13 kg/hr of high boiling condensate was separated from the bottom of the thin-film evaporator.

Isocyanate compounds including 1,3-XDI (m-XDI) were discharged through the discharge line 509 connected to the top of the thin-film evaporator 550. The high boiling material separated from the reaction product was discharged through a discharge line 506 connected to the bottom of the thin-film evaporator 550.

Example 2

An isocyanate compound including 1,3-XDI (m-XDI) was obtained in the same manner as in Example 1, except that in the scrubbing step, the temperature of the cleaning solvent supplied to the upper part of the scrubbing tower 251 was set to −5 °C.

Example 3

An isocyanate compound including 1,3-XDI (m-XDI) was obtained in the same manner as in Example 1, except that in the scrubbing step, the operating pressure of the scrubbing tower 251 was set to 730 torr.

Comparative Example 1

An isocyanate compound including 1,3-XDI (m-XDI) was obtained in the same manner as in Example 1, except that in the scrubbing step, the temperature of the cleaning solvent supplied to the upper part of the scrubbing tower 251 was set to 10 °C.

Reference Example 1

An isocyanate compound including 1,3-XDI (m-XDI) was prepared in the same manner as in Example 1, except that in the scrubbing step, the hydrochloric acid gas discharged through the column top stream line 253 was not passed through the activated carbon filter 2550.

Test Example

Part of the main stream obtained in the scrubbing step and the distillation step of Examples and Comparative Examples was recovered, and subjected to gel permeation chromatography analysis. The contents of the main components identified through the above analysis are shown in Tables 1 to 5 below.

In addition, the energy per unit time (kcal/hr) charged to the scrubbing step and the distillation step of Examples and Comparative Examples was measured, and shown in Tables 1 to 5 below.

TABLE 1

| Example 1 | Non-condensable gas discharge line 256 of scrubbing unit 250 | Phosgene discharge line 279 of distillation unit 270 | Solvent supply line 295 of distillation unit 270 |
|---|---|---|---|
| HCl (wt %) | 98.6 | 1.7 | — |
| Phosgene (wt %) | 1.4 | 97.6 | — |
| oDCB (wt %) | — | 0.70 | 100.00 |
| Energy (kcal/hr) | 350,000 | | |

TABLE 2

| Example 2 | Non-condensable gas discharge line 256 of scrubbing unit 250 | Phosgene discharge line 279 of distillation unit 270 | Solvent supply line 295 of distillation unit 270 |
|---|---|---|---|
| HCl (wt %) | 98.6 | 1.7 | — |
| Phosgene (wt %) | 1.4 | 97.6 | — |
| oDCB (wt %) | — | 0.70 | 100.00 |
| Energy (kcal/hr) | 390,000 | | |

TABLE 3

| Example 3 | Non-condensable gas discharge line 256 of scrubbing unit 250 | Phosgene discharge line 279 of distillation unit 270 | Solvent supply line 295 of distillation unit 270 |
|---|---|---|---|
| HCl (wt %) | 98.6 | 1.7 | — |
| Phosgene (wt %) | 1.4 | 97.6 | — |
| oDCB (wt %) | — | 0.70 | 100.00 |
| Energy (kcal/hr) | 330,000 | | |

TABLE 4

| Comparative Example 1 | Non-condensable gas discharge line 256 of scrubbing unit 250 | Phosgene discharge line 279 of distillation unit 270 | Solvent supply line 295 of distillation unit 270 |
|---|---|---|---|
| HCl (wt %) | 98.55 | 1.7 | — |
| Phosgene (wt %) | 1.35 | 97.9 | 0.3 |
| oDCB (wt %) | 0.1 | 0.4 | 99.7 |
| Energy (kcal/hr) | | 470,000 | |

TABLE 5

| Reference Example 1 | Non-condensable gas discharge line 256 of scrubbing unit 250 | Phosgene discharge line 279 of distillation unit 270 | Solvent supply line 295 of distillation unit 270 |
|---|---|---|---|
| HCl (wt %) | 98.6 | 1.7 | — |
| Phosgene (wt %) | 1.35 | 97.6 | — |
| oDCB (wt %) | 0.05 | 0.7 | 100 |
| Energy (kcal/hr) | | 350,000 | |

Referring to Tables 1 to 5, it was confirmed that the method for preparing an isocyanate compound according to Examples can efficiently recover and reuse phosgene used in the reaction step and a cleaning solvent used for the recovery thereof, with low energy consumption.

On the contrary, it was confirmed that in Comparative Example 1, despite the high energy consumption, the recovery efficiency of phosgene and the cleaning solvent is equivalent or lower.

The invention claimed is:

1. A method for preparing an isocyanate compound, comprising:

a reaction step of reacting a salt of amine compound with phosgene in the presence of a solvent to obtain a reaction product containing an isocyanate compound, a degassing step of removing a gas phase from the reaction product, a scrubbing step of contacting the gas phase obtained in the degassing step with a cleaning solvent having a temperature of −15 °C to 0 °C under an absolute pressure of 700 torr or more and less than 760 torr to obtain a phosgene-containing solution, a distillation step of distilling the phosgene-containing solution under normal pressure to separate the phosgene contained in the phosgene-containing solution and the cleaning solvent, a desolvation step of removing a solvent from the reaction product from which the gas phase obtained in the degassing step has been removed, a low boiling material-removing step of removing low boiling materials having a boiling point lower than that of the isocyanate compound from the reaction product from which the solvent has been removed, and a high boiling material-removing step of removing high boiling materials having a boiling point higher than that of the isocyanate compound from the reaction product from which the low boiling materials have been removed, wherein the phosgene obtained in the distillation step is supplied to the reaction step, and wherein the cleaning solvent obtained in the distillation step is supplied to the scrubbing step, wherein the desolvation step, the low boiling material-removing step, and the high boiling material-removing step are each progressed at a temperature of 165 °C or less, wherein the desolvation step is progressed at a temperature of 100 °C to 165 °C and a pressure of 30 torr or less.

2. The method of claim 1, wherein the degassing step is progressed at a temperature of 145 °C to 165 °C and a pressure of 100 torr to 600 torr.

3. The method of claim 1, wherein the cleaning solvent is at least one solvent selected from the group consisting of ethylene dichloride, monochlorobenzene, 1,2-dichlorobenzene, and 1,2,4-trichlorobenzene.

4. The method of claim 1, wherein the scrubbing step is progressed in a packed column type scrubbing tower or a multistage tray type scrubbing tower.

5. The method of claim 1, wherein the amine compound is a bifunctional amine containing two or more amino groups in its molecule.

6. The method of claim 1, wherein the amine compound is at least one alicyclic diamine selected from the group consisting of bis(aminomethyl)cyclohexane, dicyclohexylmethanediamine, cyclohexanediamine, methylcyclohexanediamine, dicyclohexyldimethylmethanediamine, and 2,2-dimethyldicyclohexylmethanediamine.

7. The method of claim 1, wherein the amine compound is at least one sulfur-containing aliphatic amine selected from the group consisting of bis(aminomethyl)sulfide, bis(aminoethyl)sulfide, bis(aminopropyl)sulfide, bis(aminohexyl)sulfide, bis(aminomethyl)sulfone, bis(aminomethyl)disulfide, bis(aminoethyl)disulfide, bis(aminopropyl)disulfide, bis(aminomethylthio)methane, bis(aminoethylthio)methane, bis(aminoethylthio)ethane, and bis(aminomethylthio)ethane.

8. The method of claim 1, wherein the amine compound is at least one aromatic xylylene diamine selected from the group consisting of m-xylylenediamine, p-xylylenediamine and o-xylylenediamine.

9. The method of claim 1, wherein the salt of amine compound is a hydrochloride or carbonic acid salt of the amine compound.

10. The method of claim 1, wherein the reaction step is progressed in the presence of a solvent containing an aromatic solvent.

11. The method of claim 10, wherein the solvent is at least one compound selected from the group consisting of monochlorobenzene, 1,2-dichlorobenzene, and 1,2,4-trichlorobenzene.

* * * * *